United States Patent

Truett

Patent Number: 5,519,220
Date of Patent: May 21, 1996

[54] FTIR CHEMICAL REACTION MONITOR

[75] Inventor: William L. Truett, West Brattleboro, Vt.

[73] Assignee: Janos Technology Inc., Townshend, Vt.

[21] Appl. No.: 267,413

[22] Filed: Jun. 28, 1994

[51] Int. Cl.⁶ .......................... G01N 21/75; G01N 21/35
[52] U.S. Cl. .................. 250/339.08; 250/339.12
[58] Field of Search .................. 250/339.07, 339.08, 250/339.12, 343; 356/440

[56] References Cited

U.S. PATENT DOCUMENTS

| | | | |
|---|---|---|---|
| 4,135,100 | 1/1979 | Harada et al. | 356/440 X |
| 4,717,827 | 1/1988 | Harvey | 250/343 |
| 4,825,076 | 4/1989 | Shields | 250/343 |
| 4,835,389 | 5/1989 | Doyle | 250/343 |
| 4,943,735 | 7/1990 | Nishikawa | 356/440 X |
| 4,998,141 | 3/1991 | Altmann | 356/440 X |
| 5,051,551 | 9/1991 | Doyle | 250/341.2 |
| 5,200,609 | 4/1993 | Sting et al. | 250/226 |
| 5,220,401 | 6/1993 | Milosevil et al. | 356/246 |

*Primary Examiner*—Carolyn E. Fields
*Assistant Examiner*—Edward J. Glick
*Attorney, Agent, or Firm*—Herbert M. Wolfson

[57] ABSTRACT

The device of the invention employs a small Teflon® vial which is mounted in a vertical position in a plastic box, and a segment of screen attached to a rod which can be raised or lowered into the reaction vessel which contains liquid reactants. When raised, the screen carries a sample into a portion of the vessel having IR transparent parts, axially aligned with corresponding parts in the plastic outer container. The device is positioned in an FTIR spectrometer. Data obtained from successive IR scans are used to follow the progress of a chemical reaction.

1 Claim, 1 Drawing Sheet

FTIR CHEMICAL REACTION MONITOR

PRIOR ART

At the present time there are several approaches to the monitoring of chemical reactions by means of using Fourier Transform Infrared (FTIR) spectrometers. In one type of device the flask containing the chemical reaction is connected to a probe which contains a fiber optic element that transfers energy from the sample compartment to the reaction vessel and then returns the acquired absorbance signal to the detector of the FTIR spectrometer. Due to the considerable loss of energy in the course of transit through the fiber optic line it is usually necessary to use a highly sensitive mercury cadmium telluride detector which must be cooled in liquid nitrogen and adds considerably to the cost of the apparatus.

A second approach to monitoring chemical reactions is to take the energy from the sample compartment of the FTIR via reflection techniques to a probe which is inserted in the reaction vessel. Usually, the energy is transmitted to an Attenuated Total Reflection (ATR) crystal at the top of the probe, which picks up an absorbance signal from the liquid in the flask with which it is in contact; energy is then returned to the spectrometer via the same reflection optics.

All schemes presently in use of fiber optic or reflection techniques are very expensive and cost thousands of dollars per unit. There are also many reactions where the chemical reactants are so corrosive that the fiber optic, or reflection, or ATR devices are destroyed.

FTIR CHEMICAL REACTION MONITOR

BACKGROUND OF THE INVENTION

The purpose of the invention is to make possible the monitoring of a chemical reaction with a very simple low cost device. The device not only has the advantage of low cost, but is also small enough that a chemical reaction carried out in the device can easily fit directly into the sample compartment of an FTIR spectrometer. Since the device is small an economical quantity of chemical reactants, milligrams instead of grams, can be utilized. The chemicals' cost and disposal problem is greatly reduced, being of great use to the hundreds of industrial and pharmaceutical and university chemists who carry out thousands of such reactions per year.

SUMMARY OF THE INVENTION

The invention employs a small reaction vessel such as a plastic vial made of Teflon®, tetrafluoroethylene polymer manufactured by E. I. duPont de Nemours & Company. The vial is mounted in a vertical position in a small plastic box. The vial is fitted with two ports to permit the passage of IR energy from an FTIR spectrometer to pass through the vial. There are also two ports in the plastic box which permit the passage of IR energy, the ports being axially aligned with the ports in the reaction vessel. There may be occasions when the ports of the vial and plastic box will be covered with IR transmitting materials, but this need not always be the case.

The plastic box can be fitted into the sample compartment of the FTIR spectrometer and secured to the spectrometer by means of a simple slide mechanism common to all spectrometers. A critical element of the invention is a small segment of screen which can be lowered into the liquid contained in the TEFLON vial reaction vessel, and raised until the screen and its liquid coating intercept the IR energy beam transiting the vial in the plastic box. The screen can be lowered or raised at will by means of its attachment to a small rod which passes through a sleeve in the top of the plastic box, and also passes through the top of the vial by means of a similar liquid tight sleeve mounted in the top cap.

The top cap of the vial containing the chemical reactants also has septa to permit the injection of reactive components into the vial, or withdrawal of solution. Heating, cooling, and stirring can also be applied to the TEFLON vial as well as a reflux condenser utilizing a hypodermic syringe with appropriate cooling. The TEFLON vial is secured to the plastic box by a simple circular metal clamp in order to maintain position.

In general a total volume of 10 ml will be easily contained and manipulated in the reactor vial. Reactions of a very wide variety can be conducted in this chemical reaction monitor, in contrast to the previously described above dependent on fiber optics or reflection techniques. The materials of construction in this monitor will not be attacked by acids, bases, or halogen reagents.

The port windows in the plastic box will consist of the appropriate IR transmitting materials, such as sodium chloride, potassium chloride, or zinc selenide. The windows are simply affixed to the box via epoxy resins. Under normal conditions the windows will not be exposed to the reagents in the TEFLON vial since the plastic box is a safety measure to protect the spectrometer.

Reactants will be introduced into the TEFLON vial reaction chamber preliminary to monitoring either by preloading or via injection. Sampling can begin post reagent addition via lowering the screen into the reaction mixture and raising the coated screen into the energy beam passing through the cell ports. Successive spectra are obtained which show the course of the reaction. As for example the hydrolysis of an organic ester by water to produce an acid and an alcohol can be followed precisely. At the conclusion of the reaction, as evidenced by no further change in the IR spectra, the reactor contents can be suitably separated into pure components via suitable techniques.

The window ports in the TEFLON vial will usually be TEFLON film which transmit most IR wavelengths, and is chemically inert; however, other materials can be used such as zinc selenide. Windows will be secured to the reaction vessel via epoxy or a pressure band to hold the film.

DETAILED DESCRIPTION OF THE PREFERRED EMBODIMENT

Figure 1:
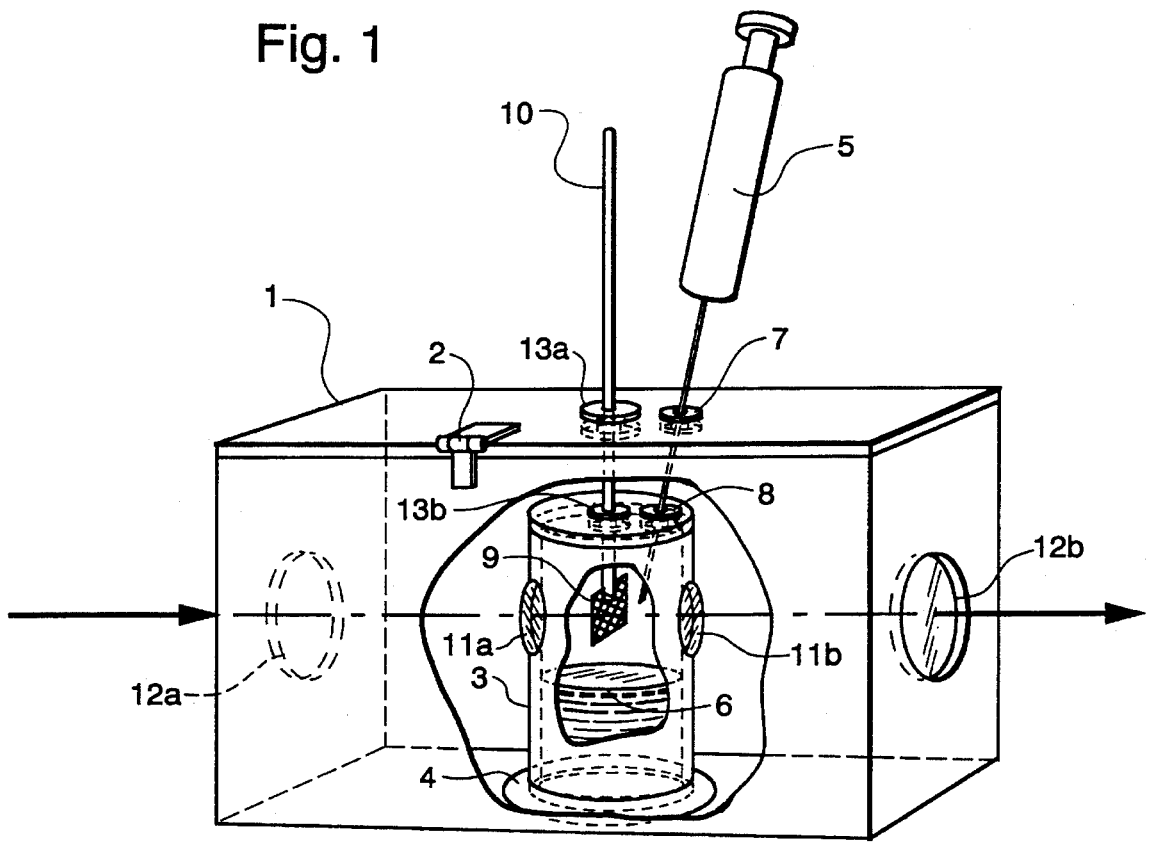
FIGURE 1 is a schematic drawing of a plastic transparent box containing a reaction vessel with screen cell.

The preferred embodiment of this invention is depicted in FIGURE 1. The plastic container 1 is a box type structure opened by a simple catch 2 to permit insertion of the reaction vessel 3 which is held in position by the clamp 4. The plastic container 1 is not necessarily fabricated from plastic and may be metal or glass but should for convenience be transparent or contain view ports.

Chemical reactants which can be a mixture of liquids and solids are placed in the reaction vessel 3 either initially or during the course of the reaction. The hypodermic syringe 5 can be used to inject reactants into the reaction vessel 3 or to remove solution 6. Access to the reaction vessel is possible through two septa, the one in the outer plastic box 7 and one at the top of the reaction vessel 3. The most critical element in the invention is the screen cell 9 which consists of a screen or grid element which is attached to a rod 10 projecting from the plastic box 1.

This rod 10 can be lowered via manual control until immersed in the liquid 6 in the reaction vessel 3, and then raised to the level of the view ports 11 permitting radiation from the spectrometer to transit the IR transmitting ports 11 in the plastic box and in the reaction vessel. In this manner a spectrum of liquid in the reaction vessel can be determined at any desired time and the progress of the reaction determined precisely.

The clamp 4 is simply held in a precise position by being epoxied to the plastic box 1. The addition of heating, cooling, and stirring devices can be done simply by the addition of small electrically powered modules available for the purpose. Also, a simple reflux condenser can be added by means of a modified hypodermic syringe inserted through the plastic box and reaction vial, however this is unnecessary with many small scale chemical reactions.

EXAMPLE 1—THE HYDROLYSIS OF ETHYL ACETATE WITH WATER USING ACID CATALYST.

5 ml of ethyl acetate was placed in the reaction vessel via access to the TEFLON reaction vessel via the front panel of the plastic box and 1.0 ml of water containing 1 drop of concentrated sulfuric acid ($H_2SO_4$) was added via the hypodermic syringe. A spectrum was immediately determined by lowering the screen cell into the reaction mixture and raising it to the level of the energy beam passing through the reaction vessel. The FTIR spectrum thus obtained indicated the presence of a strong carbonyl group (C=O) at 5.75 microns and typical water bands at 3.0 and 6.0 microns. At the completion of 1, 2, 3, and 4 hour intervals the intensity of the carbonyl group at 5.75 microns diminished progressively and at 5 hours was not present, indication completion of the hydrolysis of ethyl acetate to acetic acid and ethyl alcohol. The reaction vessel was emptied via the hypodermic syringe and processed to isolate the products.

It is obvious that many reactions will not require a protective box about the reactor vessel. However, for convenience and safety to the spectrometer it is desirable. When a non-volatile solvent and reactants are employed, as is the case with many reactions, there will be no need for IR transmitting windows in the a plastic box or the reaction vessel.

Screen materials can be selected from a wide range of materials and include screens, grids, scrim's, membranes, lattices, and the like formed from plastic, glass, ceramics, metals, and combinations of these materials.

Materials for the IR transmitting parts can be selected on the basis of the materials in the reaction vessel. For the use of acids, bases, oxidizing agents (as hydrogen peroxide), halogens and other active chemical species, fluorocarbon film offers the best chemical resistance. For the IR transmitting ports in the plastic box protecting the spectrometer, sodium chloride windows will be adequate in many cases, with zinc selenide being best for very hazardous materials.

The materials for the plastic box will depend on the nature of the temperature requirements. For ambient temperature situations, polystyrene will suffice with polyethylene as an alternate. For temperatures to 100 degrees C., polypropylene is preferred, but TEFLON boxes are available for 200–300 degrees C.

Although the main thrust of this invention is toward the use of FTIR spectrometers, the identical device of a reaction vessel with a screen cell can be used over the full range of the electromagnetic spectrum —VUV, UV, VIS, NIR, FIR— by use of the appropriate materials for each region and the appropriate spectrometer.

I claim:

1. A method for monitoring the progress of a chemical reaction using infrared spectroscopy which comprises:

a) placing a reaction vessel in the sample compartment of an FTIR spectrometer, said reaction vessel having at least two IR transparent windows facing each other in the upper section of said vessel adapted and positioned to transmit the energy beam of said spectrometer therethrough;

b) adding at least two reactant compounds to form a liquid mixture in the bottom section of said reaction vessel, each of said compounds having a unique absorbance spectrum in the IR sector of the electromagnetic spectrum;

c) agitating said mixture at a temperature sufficient to produce a reaction between said reactants and at least one reaction product;

d) inserting a screen into said mixture, said screen being constructed of a material that does not possess an absorbance spectrum in the IR sector of the electromagnetic spectrum, to provide a screen coated with said mixture;

e) raising the coated screen sufficiently to be axially disposed between said two IR transparent windows;

f) transmitting a beam of IR energy from said spectrometer through said coated screen;

g) monitoring the progress of said reaction by determining the spectrum of the liquid mixture coated on said screen from the resulting beam of IR energy that has passed through said coated screen and repeating steps (d), (e), (f) and (g) at suitable intervals until there is no further change in the spectrum of the liquid mixture on the coated screen.

* * * * *